United States Patent
Boyle

(10) Patent No.: US 12,290,685 B2
(45) Date of Patent: May 6, 2025

(54) DETECTION OF A POSITIONING STATE OF AN ELECTRODE LEAD DURING A LEAD INSERTION PROCEDURE

(71) Applicant: Advanced Bionics AG, Staefa (CH)

(72) Inventor: Patrick J. Boyle, Kent (GB)

(73) Assignee: Advanced Bionics AG, Staefa (CH)

( * ) Notice: Subject to any disclaimer, the term of this patent is extended or adjusted under 35 U.S.C. 154(b) by 552 days.

(21) Appl. No.: 17/634,066

(22) PCT Filed: Aug. 22, 2020

(86) PCT No.: PCT/IB2020/057881
§ 371 (c)(1),
(2) Date: Feb. 9, 2022

(87) PCT Pub. No.: WO2021/038416
PCT Pub. Date: Mar. 4, 2021

(65) Prior Publication Data
US 2022/0347475 A1 Nov. 3, 2022

Related U.S. Application Data

(60) Provisional application No. 62/891,054, filed on Aug. 23, 2019.

(51) Int. Cl.
*A61N 1/00* (2006.01)
*A61N 1/08* (2006.01)
(Continued)

(52) U.S. Cl.
CPC ........... *A61N 1/36038* (2017.08); *A61N 1/08* (2013.01); *A61N 1/37247* (2013.01)

(58) Field of Classification Search
CPC .................................................. A61N 1/36038
See application file for complete search history.

(56) References Cited

U.S. PATENT DOCUMENTS 8,532,781 B1 9/2013 Vanpoucke
9,959,388 B2 * 5/2018 Grandhe ................ G16H 40/63
(Continued)

FOREIGN PATENT DOCUMENTS

EP 3046618 7/2016
WO 2017160948 9/2017
(Continued)

OTHER PUBLICATIONS

"International Search Report and Written Opinion received in International Application No. PCT/IB2020/057881."
(Continued)

*Primary Examiner* — John R Downey
*Assistant Examiner* — Anant A Gupta
(74) *Attorney, Agent, or Firm* — ALG Intellectual Property, LLC

(57) ABSTRACT

An illustrative insertion management system may be configured to identify one or more attributes of a lead insertion procedure in which an electrode lead having a plurality of electrodes is inserted into a cochlea of a recipient of a cochlear implant; dynamically select, based on the one or more attributes of the lead insertion procedure, a first subset of electrodes included in the plurality of electrodes for inclusion in a monitoring electrode set, the monitoring electrode set configured to have less electrodes than a total number of the plurality of electrodes; monitor, during the lead insertion procedure, impedance values for electrodes included in the monitoring electrode set; and determine, during the lead insertion procedure and based on the monitoring, a positioning state of the electrode lead.

20 Claims, 14 Drawing Sheets

(51) Int. Cl.
*A61N 1/36* (2006.01)
*A61N 1/372* (2006.01)

(56) References Cited

U.S. PATENT DOCUMENTS

| | | | |
|---|---|---|---|
| 2010/0114288 A1* | 5/2010 | Haller | A61B 34/76 607/137 |
| 2011/0098719 A1* | 4/2011 | Llinas | A61B 34/30 607/57 |
| 2012/0316454 A1* | 12/2012 | Carter | A61N 1/0541 607/57 |
| 2014/0350640 A1* | 11/2014 | Patrick | A61N 1/0541 607/57 |
| 2015/0112408 A1 | 4/2015 | Kals | |
| 2015/0314122 A1* | 11/2015 | Kabot | A61N 1/08 607/137 |
| 2018/0050196 A1 | 2/2018 | Pawsey | |
| 2018/0140829 A1 | 5/2018 | Ramos De Miguel et al. | |
| 2019/0125226 A1* | 5/2019 | Koya | A61B 5/4839 |
| 2019/0240489 A1 | 8/2019 | Tsay | |
| 2020/0129764 A1 | 4/2020 | Johnston et al. | |

FOREIGN PATENT DOCUMENTS

| | | | |
|---|---|---|---|
| WO | 2019199333 | 10/2019 | |
| WO | WO-2019245540 A1 * | 12/2019 | A61B 5/6886 |

OTHER PUBLICATIONS

"International Search Report and Written Opinion received in International Application No. PCT/US2020/047461."

* cited by examiner

DETECTION OF A POSITIONING STATE OF AN ELECTRODE LEAD DURING A LEAD INSERTION PROCEDURE

RELATED APPLICATIONS

The present application claims priority to U.S. Provisional Patent Application No. 62/891,054, filed Aug. 23, 2019, the contents of which are hereby incorporated by reference in their entirety.

BACKGROUND INFORMATION

Correct insertion and placement of an electrode lead within a cochlea for use with a cochlear implant is of great importance for effective electrical stimulation and effective use of the cochlear implant. For example, it is important for the electrode lead to stay within the scala tympani of the cochlea instead of translocating to the scala vestibuli, to be oriented correctly (e.g., without tip foldover), and to minimize trauma to intracochlear structures so as to preserve any residual hearing that a cochlear implant recipient may have.

Unfortunately, current methods for detecting a positioning state (e.g., translocation, tip foldover, correct positioning, etc.) of an electrode lead typically involve imaging technology (e.g., x-ray technology, fluoroscopic technology, computerized tomography (CT) scanning technology, etc.) that is expensive, inconvenient, and impractical or impossible to employ in real time during lead insertion procedures.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
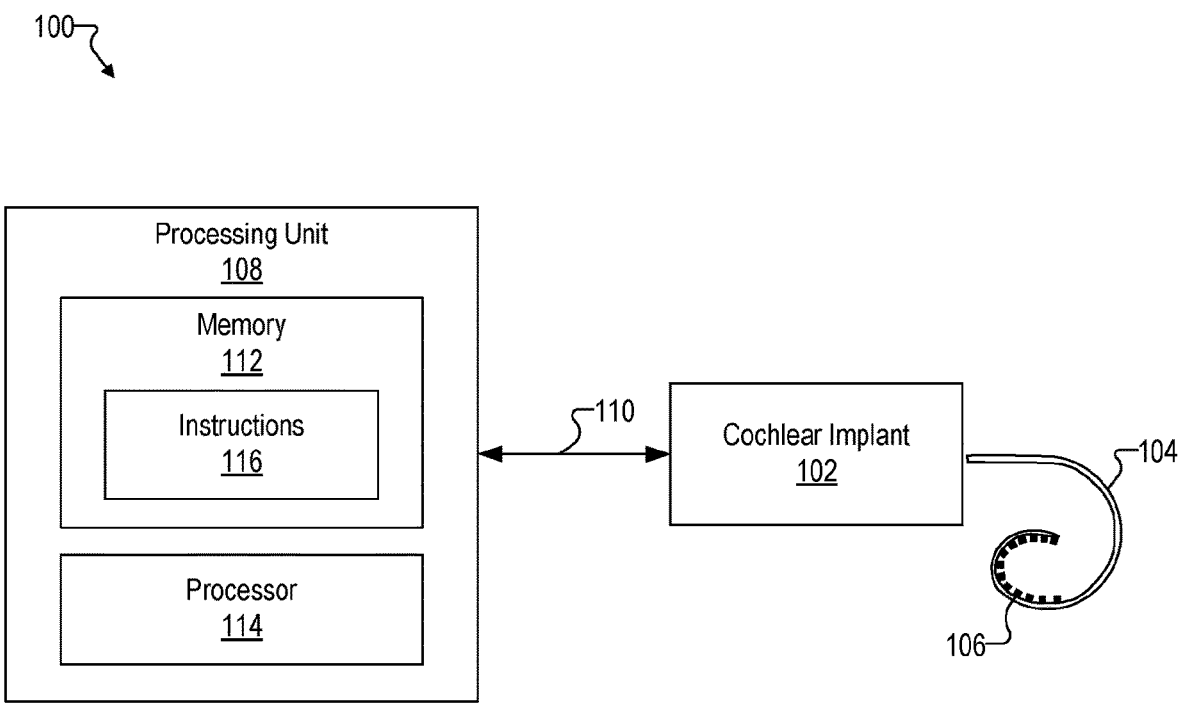
FIG. 1 illustrates an exemplary cochlear implant system.

Systems and methods for detecting a positioning state of an electrode lead during a lead insertion procedure are described herein. As used herein, a positioning state refers to any physical positioning status of an electrode lead during a lead insertion procedure. For example, the positioning state may indicate that a translocation event in which the electrode lead translocates from a first scala of the cochlea to a second scala of the cochlea is about to occur or has occurred during the lead insertion procedure. As another example, the positioning state may indicate that a tip foldover event in which a distal tip of the electrode lead folds over within the cochlea is about to occur or has occurred during the lead insertion procedure. As another example, the positioning state may indicate that that the electrode lead is correctly positioned within the cochlea during the lead insertion procedure. These and other positioning states are described more fully herein.

Detection of a positioning state of an electrode lead during a lead insertion procedure may assist in detecting potential and/or actual cochlear trauma, identifying one or more electrode positioning issues that may adversely affect performance of the electrode lead subsequent to the lead insertion procedure, and/or performing one or more remedial operations configured to correct and/or compensate for a suboptimal positioning state.

For example, during a lead insertion procedure in which an electrode lead is inserted into a cochlea, the electrode lead may travel into the scala tympani of the cochlea but, instead of continuing to travel through the scala tympani, may inadvertently puncture the basilar membrane and/or other anatomy separating the scala tympani from the scala vestibuli to enter the scala vestibuli. Because such a scalar translocation may damage the basilar membrane and hair cells disposed on the basilar membrane, the translocation of the electrode lead may cause trauma to the cochlea and potentially adversely affect the recipient's residual hearing, provoke more reaction to the foreign body (e.g., the electrode lead), produce more fibrous sheath, increase impedances, and/or lead to the loss of cochlear tissue that could have an adverse effect on use of the cochlear implant.

As another example, during a lead insertion procedure in which an electrode lead is inserted into a cochlea, a distal portion of the electrode lead may undesirably fold over such that one or more electrodes on the distal portion of the electrode lead are incorrectly positioned in the cochlea (e.g., the distal-most electrode on the electrode lead may be adjacent to one of the electrodes in a middle region of the electrode lead). This may adversely affect representation of sound to the recipient by way of the electrodes.

Systems and methods described herein are configured to detect scalar translocation, tip foldover, and/or other positioning states of an electrode lead in real time during a lead insertion procedure and/or after the lead insertion procedure (e.g., so that the insertion states may be associated with data being studied to help reduce trauma and improve outcomes in subsequent lead insertion procedures, or for other suitable purposes as described herein).

Systems and methods described herein for detecting insertion states of an electrode lead within a cochlea of a cochlear implant recipient may provide various benefits to cochlear implant recipients, as well as to surgeons and others involved with insertion procedures. For example, by providing real time information about whether a translocation event, a tip foldover event, and/or other undesirable electrode positioning event is about to occur and/or has occurred during the lead insertion procedure, disclosed systems and methods may provide a surgeon or other user performing the lead insertion procedure with information and perspective into the intricate insertion procedure, thereby allowing for a positioning of the electrode lead to be corrected (e.g., withdrawn and reinserted without scalar translocation or tip foldover) or for trauma to otherwise be mitigated to facilitate a successful outcome of the lead insertion procedure.

Even after an insertion procedure is complete, disclosed systems and methods for detecting a positioning state of an electrode lead may be useful for providing insight into a final resting location at which the electrode lead has been inserted.

Additionally, regardless of whether disclosed system and methods for detecting a positioning state of an electrode lead are performed in real time during a lead insertion procedure or after the fact when the electrode lead is stationary, the detecting of electrode lead positioning state without use of expensive, inconvenient, or risky imaging technology (e.g., x-ray technology, fluoroscopic technology, CT scanning technology, etc.) may be beneficial. For example, by detecting a positioning state of an electrode lead while avoiding these other technologies, recipients may be less exposed to various risks, inconveniences, costs, and/or other undesirable aspects associated with such technology.

Moreover, by dynamically selecting which electrodes to include in a monitoring electrode set based on one or more attributes of the lead insertion procedure, systems and methods described herein may increase the probability that a positioning state of the electrode lead is correctly identified. Reasons for this are described herein.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100 configured to be used by a recipient. As shown, cochlear implant system 100 includes a cochlear implant 102, an electrode lead 104 physically coupled to cochlear implant 102 and having an array of electrodes 106, and a processing unit 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and electrode leads for each ear of the recipient. In the bilateral configuration, processing unit 108 may be implemented by a single processing unit configured to interface with both cochlear implants or by two separate processing units each configured to interface with a different one of the cochlear implants.

Cochlear implant 102 may be implemented by any suitable type of implantable stimulator. For example, cochlear implant 102 may be implemented by an implantable cochlear stimulator. Additionally or alternatively, cochlear implant 102 may be implemented by a brainstem implant and/or any other type of device that may be implanted within the recipient and configured to apply electrical stimulation to one or more stimulation sites located along an auditory pathway of the recipient.

In some examples, cochlear implant 102 may be configured to generate electrical stimulation representative of an audio signal (also referred to herein as audio content) processed by processing unit 108 in accordance with one or more stimulation parameters transmitted to cochlear implant 102 by processing unit 108. Cochlear implant 102 may be further configured to apply the electrical stimulation to one or more stimulation sites (e.g., one or more intracochlear locations) within the recipient by way of one or more electrodes 106 on electrode lead 104. In some examples, cochlear implant 102 may include a plurality of independent current sources each associated with a channel defined by one or more of electrodes 106. In this manner, different stimulation current levels may be applied to multiple stimulation sites simultaneously by way of multiple electrodes 106.

Cochlear implant 102 may additionally or alternatively be configured to generate, store, and/or transmit data. For example, cochlear implant may use one or more electrodes 106 to record one or more signals (e.g., one or more voltages, impedances, evoked responses within the recipient, and/or other measurements) and transmit, by way of communication link 110, data representative of the one or more signals to processing unit 108. In some examples, this data is referred to as back telemetry data.

Electrode lead 104 may be implemented in any suitable manner. For example, a distal portion of electrode lead 104 may be pre-curved such that electrode lead 104 conforms with the helical shape of the cochlea after being implanted. Electrode lead 104 may alternatively be naturally straight or of any other suitable configuration.

In some examples, electrode lead 104 includes a plurality of wires (e.g., within an outer sheath) that conductively couple electrodes 106 to one or more current sources within cochlear implant 102. For example, if there are n electrodes 106 on electrode lead 104 and n current sources within cochlear implant 102, there may be n separate wires within electrode lead 104 that are configured to conductively connect each electrode 106 to a different one of the n current sources. Exemplary values for n are 9, 12, 16, or any other suitable number.

Electrodes 106 are located on at least a distal portion of electrode lead 104. In this configuration, after the distal portion of electrode lead 104 is inserted into the cochlea, electrical stimulation may be applied by way of one or more of electrodes 106 to one or more intracochlear locations. One or more other electrodes (e.g., including a ground electrode, not explicitly shown) may also be disposed on other parts of electrode lead 104 (e.g., on a proximal portion of electrode lead 104) to, for example, provide a current return path for stimulation current applied by electrodes 106 and to remain external to the cochlea after the distal portion of electrode lead 104 is inserted into the cochlea. Additionally or alternatively, a housing of cochlear implant 102 may serve as a ground electrode for stimulation current applied by electrodes 106.

Processing unit 108 may be configured to interface with (e.g., control and/or receive data from) cochlear implant 102. For example, processing unit 108 may transmit commands (e.g., stimulation parameters and/or other types of operating parameters in the form of data words included in a forward telemetry sequence) to cochlear implant 102 by way of communication link 110. Processing unit 108 may additionally or alternatively provide operating power to cochlear implant 102 by transmitting one or more power signals to cochlear implant 102 by way of communication link 110. Processing unit 108 may additionally or alternatively receive data from cochlear implant 102 by way of communication link 110. Communication link 110 may be implemented by any suitable number of wired and/or wireless bidirectional and/or unidirectional links.

As shown, processing unit 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable medium and/or non-transitory processor-readable medium, such as any combination of non-volatile storage media and/or volatile storage media, Exemplary non-volatile storage media include, but are not limited to, read-only memory, flash memory, a solid-state drive, a magnetic storage device (e.g., a hard drive), ferro-electric random-access memory ("RAW"), and an optical disc. Exemplary volatile storage media include, but are not limited to, RAM (e.g., dynamic RAM).

Memory 112 may maintain (e.g., store) executable data used by processor 114 to perform one or more of the operations described herein as being performed by processing unit 108. For example, memory 112 may store instructions 116 that may be executed by processor 114 to perform any of the audio content processing and cochlear implant control operations described herein. Instructions 116 may be implemented by any suitable application, program (e.g., sound processing program), software, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102.

To illustrate, processor 114 may be configured to control an operation of cochlear implant 102. For example, processor 114 may receive an audio signal (e.g., by way of a microphone communicatively coupled to processing unit 108, a wireless interface (e.g., a Bluetooth interface), and/or a wired interface (e.g., an auxiliary input port)). Processor 114 may process the audio signal in accordance with a sound processing strategy (e.g., a sound processing program stored in memory 112) to generate appropriate stimulation parameters. Processor 114 may then transmit the stimulation parameters to cochlear implant 102 to direct cochlear implant 102 to apply electrical stimulation representative of the audio signal to the recipient.

Processor 114 may be additionally or alternatively configured to receive and process data generated by cochlear implant 102. For example, processor 114 may receive data representative of a signal recorded by cochlear implant 102 using one or more electrodes 106 and, based on the data, adjust one or more operating parameters of processing unit 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by processing unit 108 and/or any implementation thereof may be understood to be performed by processor 114 based on instructions 116 stored in memory 112.

Figure 2:
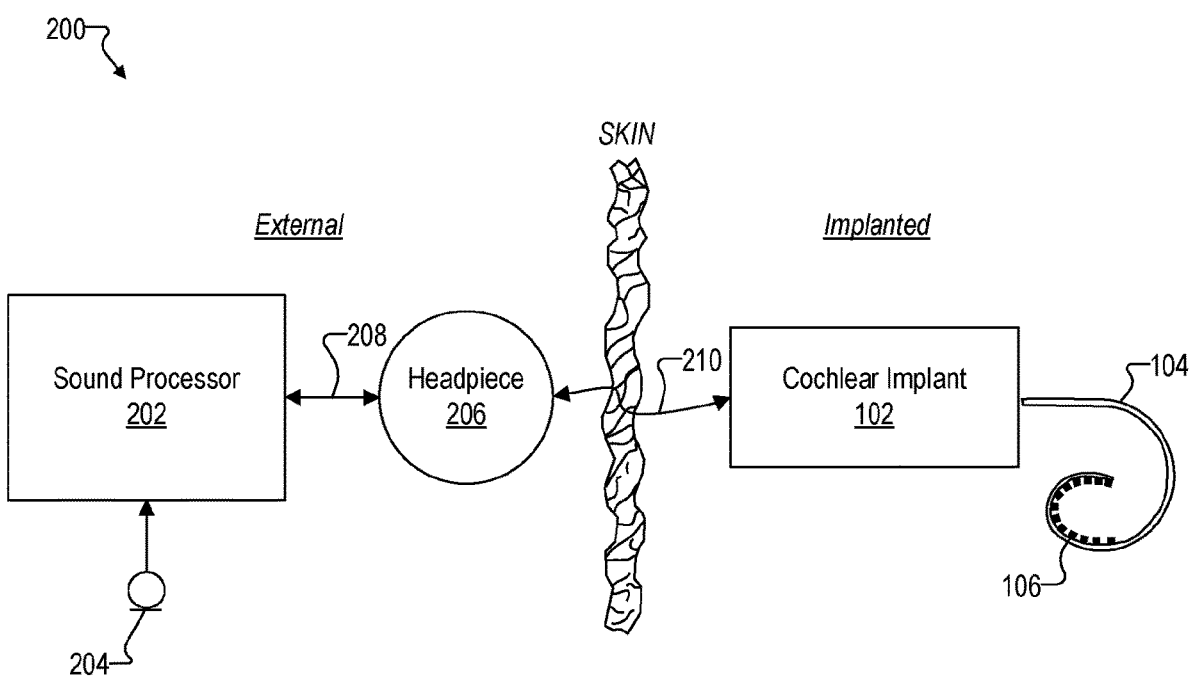
FIG. 2 shows an exemplary configuration of the cochlear implant system of FIG. 1.

Processing unit 108 may be implemented by one or more devices configured to interface with cochlear implant 102. To illustrate, FIG. 2 shows an exemplary configuration 200 of cochlear implant system 100 in which processing unit 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear ("BTE") unit configured to be worn behind and/or on top of an ear of the recipient. Additionally or alternatively, sound processor 202 may be implemented by an off-the-ear unit (also referred to as a body worn device) configured to be worn or carried by the recipient away from the ear. Additionally or alternatively, at least a portion of sound processor 202 is implemented by circuitry within headpiece 206.

Microphone 204 is configured to detect one or more audio signals (e.g., that include speech and/or any other type of sound) in an environment of the recipient.

Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone as may serve a particular implementation.

Headpiece 206 may be selectively and communicatively coupled to sound processor 202 by way of a communication link 208 (e.g., a cable or any other suitable wired or wireless communication link), which may be implemented in any suitable manner. Headpiece 206 may include an external antenna (e.g., a coil and/or one or more wireless communication components) configured to facilitate selective wireless coupling of sound processor 202 to cochlear implant 102. Headpiece 206 may additionally or alternatively be used to selectively and wirelessly couple any other external device to cochlear implant 102. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise connected to cochlear implant 102. In this manner, stimulation parameters and/or power signals may be wirelessly and transcutaneously transmitted between sound processor 202 and cochlear implant 102 by way of a wireless communication link 210.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply electrical stimulation representative of the audio signal to the recipient.

In an alternative configuration, sound processor 202 may be implanted within the recipient instead of being located external to the recipient. In this alternative configuration, which may be referred to as a fully implantable configuration of cochlear implant system 100, sound processor 202 and cochlear implant 102 may be combined into a single device or implemented as separate devices configured to communicate one with another by way of a wired and/or wireless communication link. In a fully implantable implementation of cochlear implant system 100, headpiece 206 may not be included and microphone 204 may be implemented by one or more microphones implanted within the recipient, located within an ear canal of the recipient, and/or external to the recipient.

Figure 3:
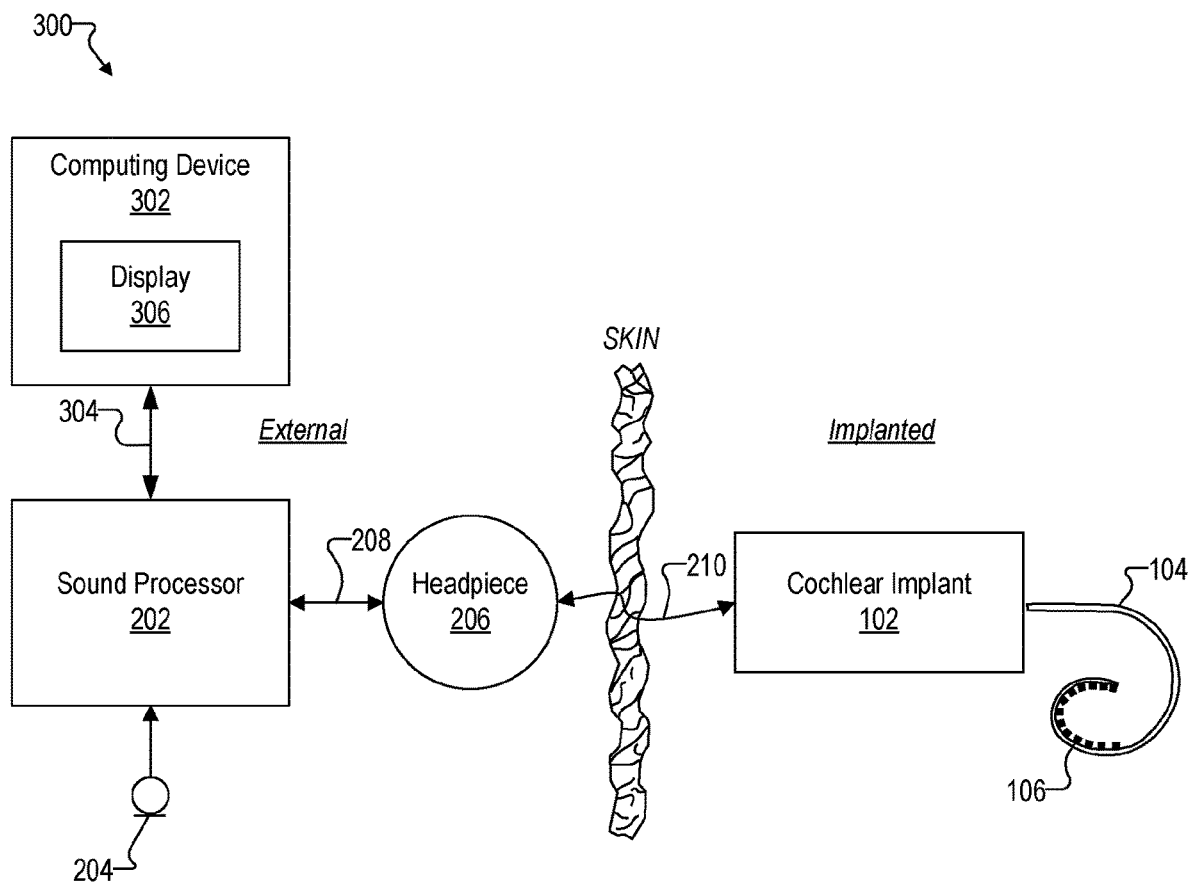
FIG. 3 shows another exemplary configuration of the cochlear implant system of FIG. 1.

FIG. 3 shows an exemplary configuration 300 of cochlear implant system 100 in which processing unit 108 is implemented by a combination of sound processor 202 and a computing device 302 configured to communicatively couple to sound processor 202 by way of a communication link 304, which may be implemented by any suitable wired or wireless communication link.

Computing device 302 may be implemented by any suitable combination of hardware and software. To illustrate, computing device 302 may be implemented by a mobile device (e.g., a mobile phone, a laptop, a tablet computer, etc.), a desktop computer, and/or any other suitable computing device as may serve a particular implementation. As an example, computing device 302 may be implemented by a mobile device configured to execute an application (e.g., a "mobile app") that may be used by a user (e.g., the recipient, a clinician, and/or any other user) to control one or more settings of sound processor 202 and/or cochlear implant 102 and/or perform one or more operations (e.g., diagnostic operations) with respect to data generated by sound processor 202 and/or cochlear implant 102.

In some examples, computing device 302 may be configured to control an operation of cochlear implant 102 by transmitting one or more commands to cochlear implant 102 by way of sound processor 202. Likewise, computing device 302 may be configured to receive data generated by cochlear implant 102 by way of sound processor 202. Alternatively, computing device 302 may interface with (e.g., control and/or receive data from) cochlear implant 102 directly by way of a wireless communication link between computing device 302 and cochlear implant 102. In some implementations in which computing device 302 interfaces directly with cochlear implant 102, sound processor 202 may or may not be included in cochlear implant system 100.

Computing device 302 is shown as having an integrated display 306. Display 306 may be implemented by a display screen, for example, and may be configured to display content generated by computing device 302. Additionally or alternatively, computing device 302 may be communicatively coupled to an external display device (not shown) configured to display the content generated by computing device 302.

In some examples, computing device 302 represents a fitting device configured to be selectively used (e.g., by a clinician) to fit sound processor 202 and/or cochlear implant 102 to the recipient. In these examples, computing device 302 may be configured to execute a fitting program configured to set one or more operating parameters of sound processor 202 and/or cochlear implant 102 to values that are optimized for the recipient. As such, in these examples, computing device 302 may not be considered to be part of cochlear implant system 100. Instead, computing device 302 may be considered to be separate from cochlear implant system 100 such that computing device 302 may be selectively coupled to cochlear implant system 100 when it is desired to fit sound processor 202 and/or cochlear implant 102 to the recipient.

Figure 4:
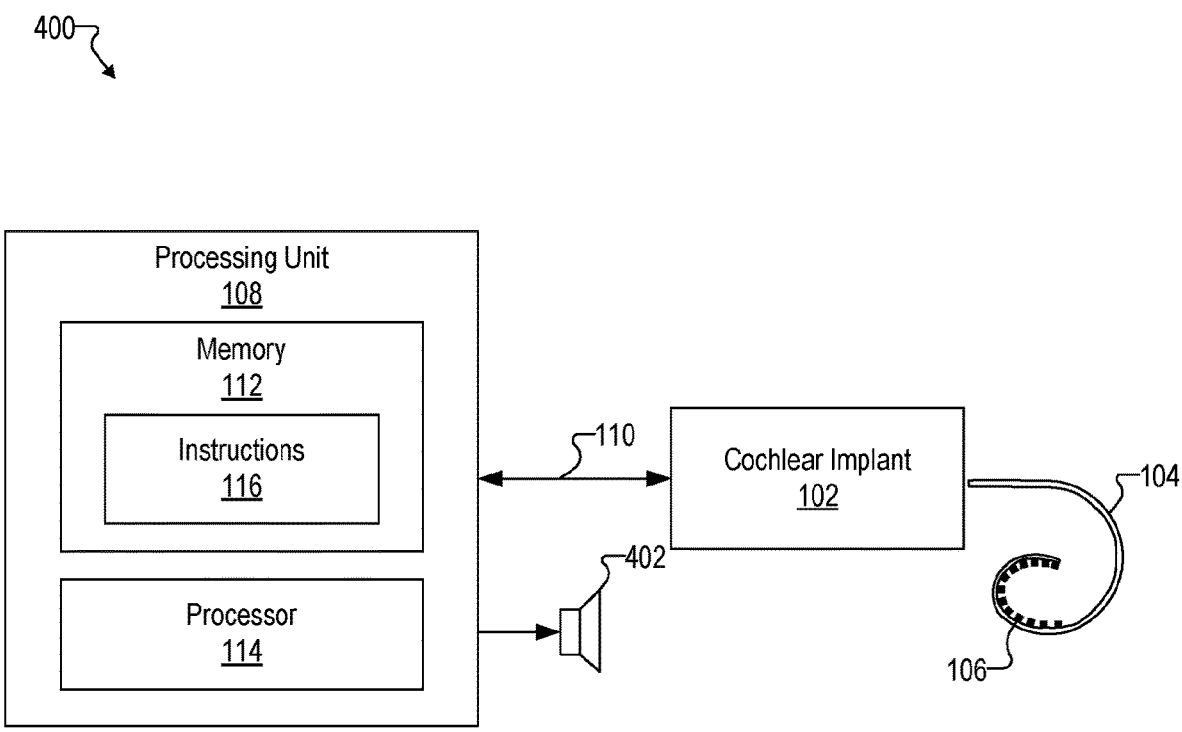
FIG. 4 shows another exemplary configuration of the cochlear implant system of FIG. 1.

In some implementations, processing unit 108 may also be configured to apply acoustic stimulation to the recipient. For example, FIG. 4 shows an exemplary configuration 400 in which a receiver 402 (also referred to as a loudspeaker) may be coupled to processing unit 108. Receiver 402 may be coupled to processing unit 108 in any suitable manner. For example, receiver 402 may be coupled directly to sound processor 202 or to computing device 302.

In configuration 400, processing unit 108 may deliver acoustic stimulation to the recipient by way of receiver 402. The acoustic stimulation may be representative of an audio signal (e.g., an amplified version of the audio signal) configured to elicit an evoked response within the recipient and/or otherwise configured. In configurations in which processing unit 108 is configured to both deliver acoustic stimulation to the recipient and direct cochlear implant 102 to apply electrical stimulation to the recipient, cochlear implant system 100 may be referred to as a bimodal hearing system and/or any other suitable term.

Figure 5:
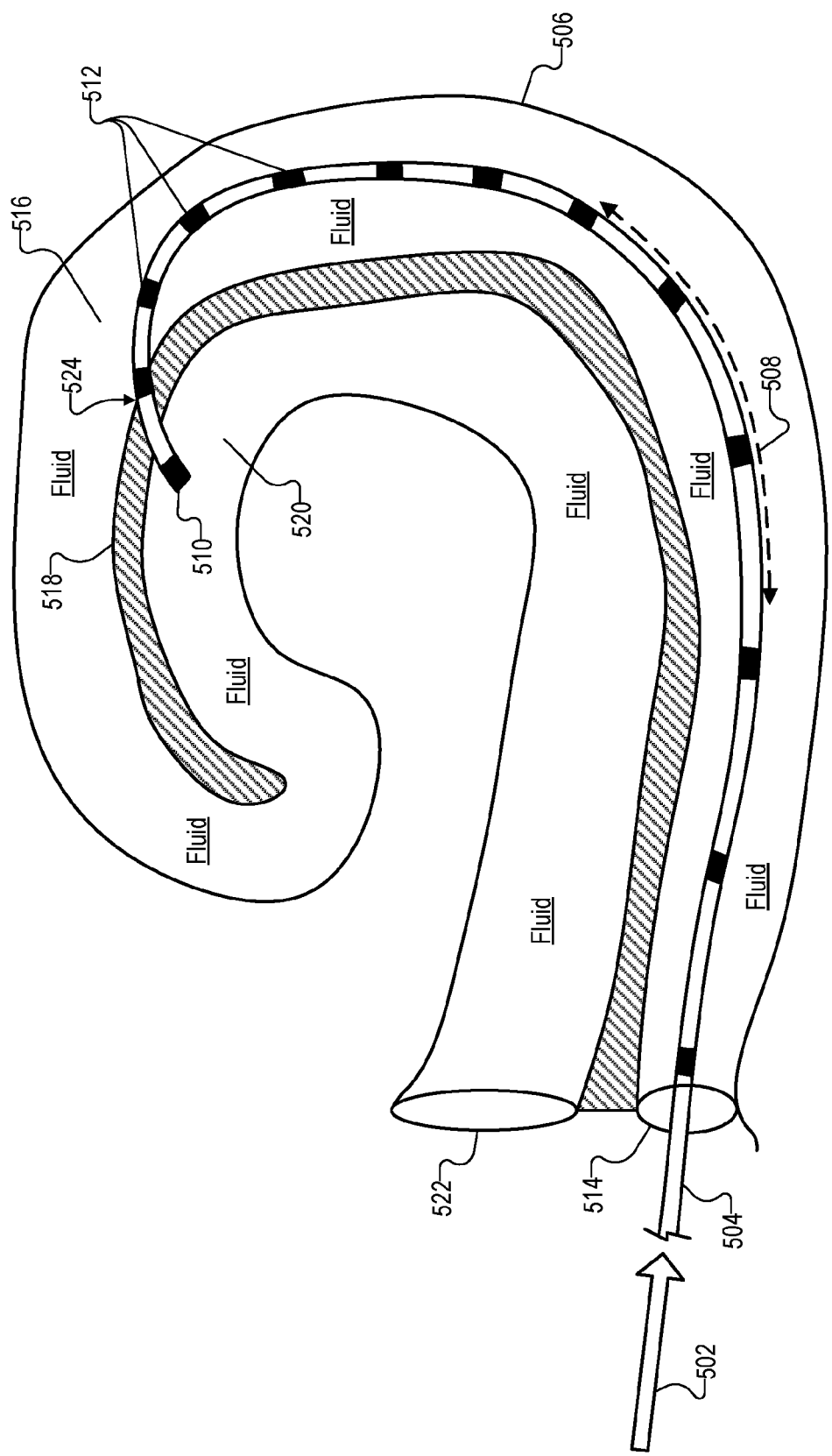
FIGS. 5-6 show exemplary aspects of an electrode lead and of recipient anatomy as an exemplary insertion procedure is performed.

To illustrate the context in which a lead insertion procedure (or simply "insertion procedure") is performed and how a scalar translocation of an electrode lead may occur, FIG. 5 shows exemplary aspects of an electrode lead and of recipient anatomy as an exemplary insertion procedure is performed, Specifically, as shown, an insertion procedure 502 is illustrated in which a distal portion of an electrode lead 504 is inserted into a cochlea 506 of a recipient along an insertion path 508 (which is illustrated in part by a dashed curve but will be understood to including the entire path taken by electrode lead 504 within cochlea 506). It will be understood that, while only a distal portion of electrode lead 504 is illustrated in FIG. 5, a proximal portion of the electrode lead not explicitly shown may be coupled to a cochlear implant (also not shown) that may direct current into electrode lead 504, receive and pass on data detected by electrode lead 504 (e.g., evoked response data or the like), and so forth.

As shown, electrode lead 504 may include various electrodes including a leading electrode 510 (also referred to as a most apical electrode) nearest a distal end of electrode lead 504 and several additional electrodes 512 disposed along the length of electrode lead 504. Unless the context dictates otherwise, it will be understood that electrodes 512, when referred to generally herein, may include all the electrodes disposed on electrode lead 504 including electrode 510 and/or electrodes not explicitly shown in FIG. 5.

As shown, electrode 510 is located at a distal end of lead 504. Thus, electrode 510 may be referred to as a "tip electrode". Alternatively, the distal-most electrode on lead 504 may not be located at the very distal end of lead 504. In these examples, the tip of lead 504 may be made out of silicone or some other insulative material. In cases where electrode 510 is a tip electrode, the tip electrode may be smaller than the other electrodes on lead 504 and may therefore have a higher impedance to start out with. This difference in size and impedance may be corrected or compensated for during the various impedance measurement techniques described herein.

As illustrated in FIG. 5, insertion procedure 502 may involve inserting electrode lead 504 through an entry point 514 (e.g., within a round window or cochleostomy of cochlea 506, or another suitable location) and into a scala tympani 516 of cochlea 506, Scala tympani 516 is a chamber of cochlea 506 that is separated by a basilar membrane 518 (e.g., as well as other membranes and anatomical structures not explicitly shown or labeled in FIG. 5) from a scala vestibuli 520 of cochlea 506 (i.e., a separate chamber of the cochlea). As such, vibrations introduced at an oval window 522 of cochlea 506 may vibrate through fluid included in scala vestibuli 520 toward the apex of cochlea 506 and back toward the base of cochlea 506 through fluid included in scala tympani 516. In other words, sound vibrations traveling on either side of basilar membrane 518 may be moving in opposite directions and, as such, may be out of phase with one another. As the vibrations travel through fluid in scala tympani 516, the vibrations may be detected and encoded by hair cells along basilar membrane 518 (if undamaged hair cells are present in the particular recipient). Additionally or alternatively, electrodes 512 disposed throughout scala tympani 516 may generate electrical stimulation to stand in for the function of damaged hair cells. Regardless, nerves associated with different depths (frequency regions) along cochlea 506 may send signals to the brain to effect a hearing sensation.

FIG. 5 illustrates electrode lead 504 within cochlea 506 at a particular moment during insertion procedure 502. Specifically, at the moment depicted in FIG. 5, electrode lead 504 has translocated from scala tympani 516, through basilar membrane 518, and into scala vestibuli 520 at a translocation site 524. This scalar translocation of electrode lead 504 may have occurred for any of a variety of reasons during insertion procedure 502, but is most likely an undesirable occurrence because, as shown, the distal end of electrode lead 504 (i.e., at leading electrode 510) has physically penetrated basilar membrane 518, thereby potentially causing trauma to basilar membrane 518 and/or any of various other parts of cochlea 506 associated with basilar membrane 518 (e.g., previously functional hair cells along basilar membrane 518, other membranes or nerves associated with basilar membrane 518, etc.).

Figure 6:
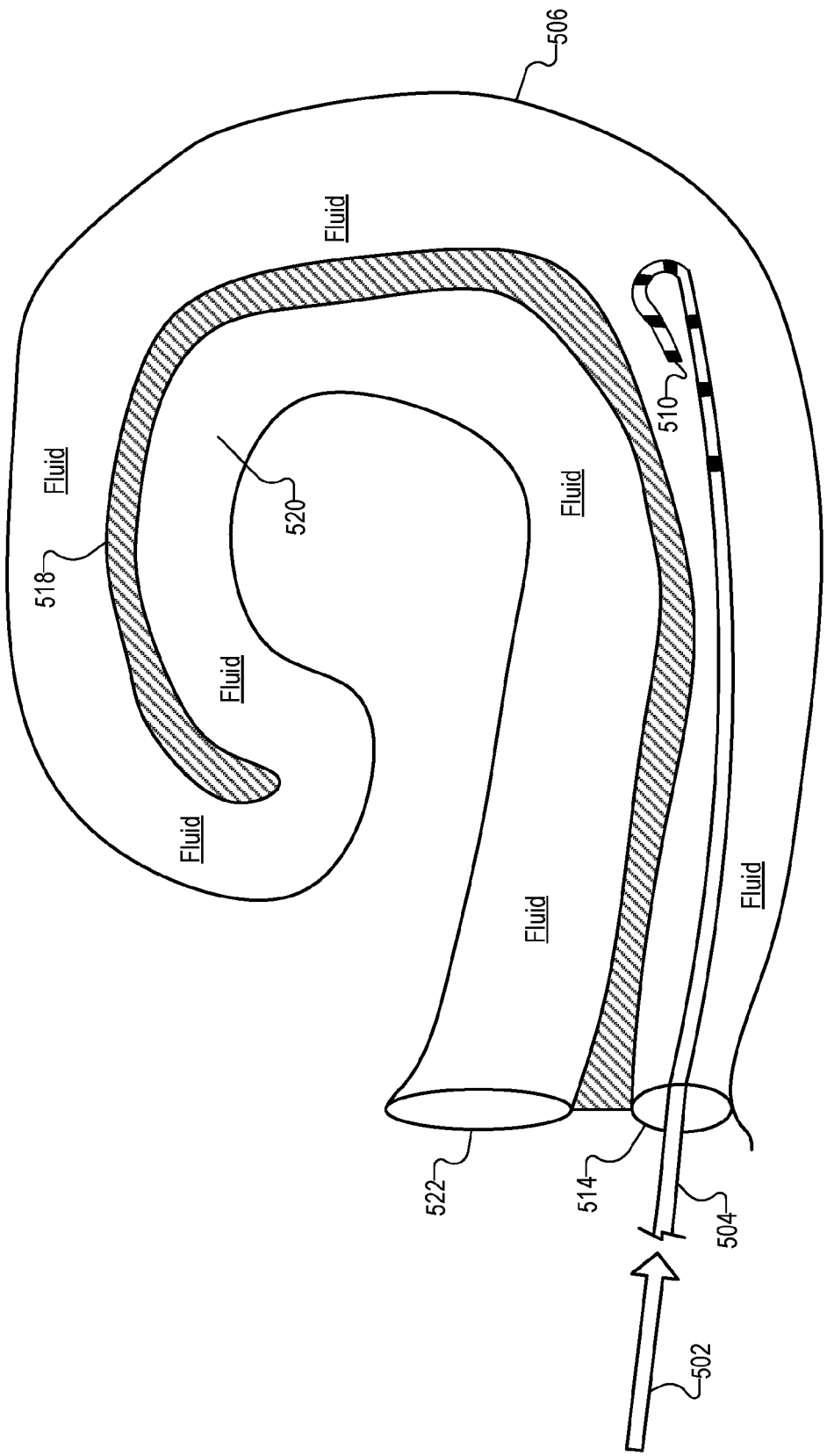

FIG. 6 is similar to FIG. 5, but shows an illustrative tip foldover event. In particular, as shown, a distal end of electrode lead 504 has folded over such that electrode 510 and other electrodes towards the distal end of electrode lead 504 are incorrectly positioned within cochlea 506. Tip foldover may adversely affect delivery of sound to the recipient, as one or more electrodes are not appropriately positioned within the cochlea 506.

Figure 7:
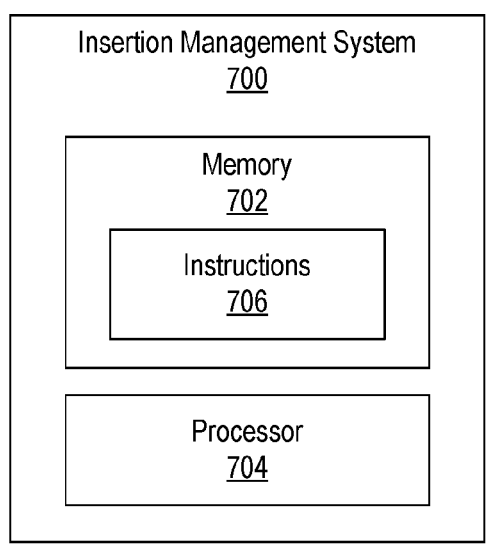
FIG. 7 shows an exemplary insertion management system.

FIG. 7 shows an exemplary insertion management system 700 ("system 700") that may be configured to perform various operations with respect to a lead insertion procedure. For example, system 700 may be configured to detect one or more positioning states of an electrode lead (e.g., lead 104 or lead 504) during a lead insertion procedure. By detecting positioning states, system 700 may be configured to ensure or increase the likelihood of a successful outcome for the lead insertion procedure.

System 700 may be implemented by one or more computing devices, such as any of the computing devices described herein (e.g., processing unit 108, sound processor 202, and/or computing device 302) and/or any computing device not included in cochlear implant system 100. For example, system 700 may be implemented by one or more computing devices accessible by a user before and/or during a lead insertion procedure and/or one or more servers located remote from an intraoperative space associated with the lead insertion procedure. System 700 may be maintained and/or otherwise associated with a manufacturer of cochlear implant systems, a provider of cochlear implant systems, a surgical center where lead insertion procedures are performed, and/or any other entity as may serve a particular implementation.

As shown, system 700 includes a memory 702 and a processor 704 configured to be selectively and communicatively coupled to one another. In some examples, memory 702 and processor 704 may be distributed between multiple devices and/or multiple locations as may serve a particular implementation.

Memory 702 may be implemented by any suitable non-transitory computer-readable medium and/or non-transitory processor-readable medium, such as any combination of non-volatile storage media and/or volatile storage media as described herein.

Memory 702 may maintain (e.g., store) executable data used by processor 704 to perform one or more of the operations described herein as being performed by system 700. For example, memory 702 may store instructions 706 that may be executed by processor 704 to perform any of the machine learning model operations described herein. Instructions 706 may be implemented by any suitable application, program, software, code, and/or other executable data instance. Memory 702 may also maintain any data received, generated, managed, used, and/or transmitted by processor 704.

Processor 704 may be configured to perform (e.g.; execute instructions 706 stored in memory 702 to perform) various operations with respect to detecting a positioning state of an electrode lead. In the description provided herein, any references to operations performed by system 700 and/or any implementation thereof may be understood to be performed by processor 704 based on instructions 706 stored in memory 702.

When translocation, tip foldover, or other undesirable electrode lead positioning events occur, an impedance value for an affected electrode (i.e., an electrode located on a portion of an electrode lead that has translocated or folded over) may change (e.g., increase) relative to the trend of other electrodes on the electrode lead. System 700 may accordingly be configured to monitor impedance values for one or more electrodes during the lead insertion procedure. Based on the monitoring, system 700 may determine a positioning state of the electrode lead. Examples of this are described herein.

In some examples, system 700 may be configured to monitor impedance values for electrodes include in a monitoring electrode set. As used herein, a monitoring electrode set refers to a dynamically selected group of electrodes on an electrode lead, where a total number of electrodes in the monitoring electrode set is less than a total number of electrodes on the entire electrode lead. Monitoring impedance values for electrodes included in the monitoring electrode set may be faster and less resource intensive than conventional techniques that perform impedance measurements on all of the electrodes on the electrode lead.

Any suitable number of electrodes may be included in the electrode monitoring set, as long as the number is less than the total number of electrodes on the electrode lead. For example, the electrode monitoring set may include only one, only two, only three, or only four electrodes. The electrodes selected for inclusion in the electrode monitoring set may be adjacent one to another and/or non-adjacent.

Figure 8:
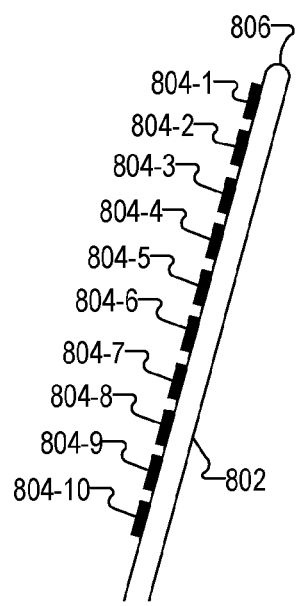
FIG. 8 shows a distal portion of an electrode lead.

To illustrate, reference is made to FIG. 8, which shows a distal portion of an electrode lead 802 with a plurality of electrodes 804 (e.g., electrodes 804-1 through 804-10) disposed thereon, Electrode 804-1 is a distal-most electrode on lead 802 located closest to a distal end 806 of lead 802. The number of electrodes 804 shown as being disposed on lead 802 is exemplary only, and has been limited to simplify the following discussion. Any suitable number of electrodes 804 (e.g., sixteen) may be included on lead 802 without departing from the scope of the present disclosure. Electrode lead 802 and electrodes 804 may be similar to any of the electrode leads and electrodes described herein.

Depending on one or more attributes of the lead insertion procedure, it may be more beneficial to monitor impedance values for certain electrodes on an electrode lead than other electrodes on the electrode lead. For example, at the beginning of a lead insertion procedure, it may be most beneficial to monitor impedance values for electrodes located near a distal end of the electrode lead (e.g., electrodes 804-1 through 804-4). However, subsequently, it may be most beneficial to monitor impedance values for electrodes located more towards a middle or proximal portion of the electrode lead (e.g., electrodes 804-4 through 804-7). For example, as the electrode lead reaches the first basal turn of the cochlea, the distal end of the electrode lead may become inadvertently lodged in the side wall of the cochlea, thereby causing a middle portion of the electrode lead to bow out and translocate from one scala to another scala. In this situation, it may be more beneficial to monitor impedance values for electrodes located in the middle portion of the electrode lead. Other combinations of attributes of the lead insertion procedure may otherwise affect which electrodes should be included in the monitoring electrode set.

System 700 may accordingly be configured to identify one or more attributes of a lead insertion procedure in which an electrode lead having a plurality of electrodes is inserted into a cochlea of a recipient of a cochlear implant and dynamically select, based on the one or more attributes of the lead insertion procedure, a subset of electrodes included in the plurality of electrodes for inclusion in the monitoring electrode set. System 700 may then monitor, during the lead insertion procedure, impedance values for electrodes included in the monitoring electrode set. As one or more attributes of the lead insertion procedure change over time, system 700 may dynamically select a different subset of electrodes for inclusion in the monitoring electrode set.

Figure 9:
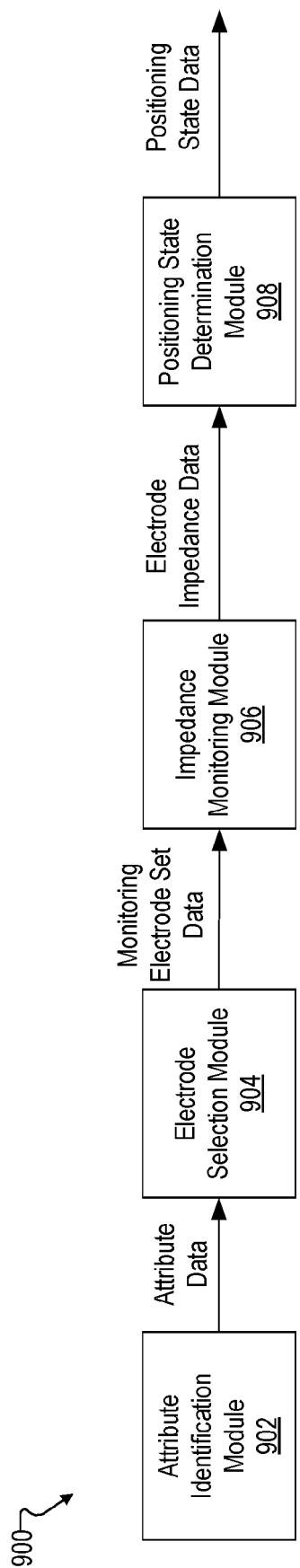
FIGS. 9-10 show exemplary implementations of the system of FIG. 7.

To illustrate, FIG. 9 shows an exemplary implementation 900 of system 700. As shown, implementation 900 includes an attribute identification module 902, an electrode selection module 904, an impedance monitoring module 906, and a positioning state determination module 908. Each module shown in FIG. 9 may be implemented by any suitable combination of hardware and/or software.

Attribute identification module 902 may be configured to identify one or more attributes of a lead insertion procedure in which an electrode lead having a plurality of electrodes is inserted into a cochlea of a recipient of a cochlear implant. The one or more attributes may be identified prior to a commencement of the lead insertion procedure and/or during the lead insertion procedure. As shown, attribute identification module 902 may output attribute data representative of the one or more attributes. Exemplary attributes that may be represented by attribute data are described herein.

Electrode selection module 904 is configured to receive attribute data and, based on the attribute data, select a subset of electrodes included in the plurality of electrodes for inclusion in a monitoring electrode set. Electrode selection module 904 may output monitoring electrode set data representative of the selected electrodes.

Impedance monitoring module 906 may be configured to perform any of the electrode impedance monitoring operations described herein. For example, impedance monitoring module 906 may be configured to monitor, during the lead insertion procedure, impedance values for the electrodes included in the monitoring electrode set. As shown, impedance monitoring module 906 may be configured to output electrode impedance data, which is representative of the impedance values of the electrodes included in the monitoring electrode set.

Positioning state determination module 908 is configured to determine, based on the electrode impedance data, a positioning state of the electrode lead. Positioning state determination module 908 may output positioning state data representative of the determined positioning state.

Various examples of attribute data that may be generated by system 700 (e.g., attribute identification module 902) will now be described. The attributes represented by the attribute data described herein are merely illustrative of the many different attributes that may be identified and used to select electrodes for inclusion in the monitoring electrode set.

In some examples, the attribute data may be representative of one or more characteristics (e.g., a make, model, type, size, flexibility rating, etc.) of the electrode lead being inserted into the cochlea and/or a tool being used to insert the electrode lead into the cochlea.

The attribute data may additionally or alternatively be representative of one or more characteristics of an opening in the recipient through which the electrode lead is to be inserted. For example, the attribute data may be representative of a location and/or a size of the opening.

The attribute data may additionally or alternatively be representative of an identity of a user performing or otherwise associated with the lead insertion procedure. For example, the attribute data may be representative of a user ID associated with a surgeon who performs the lead insertion procedure. This user ID may be used to access historical data associated with the user to determine one or more surgical tendencies of the user (e.g., electrode lead preferences, tool preferences, recipient positioning preferences, etc.). These tendencies may affect an outcome of the lead insertion procedure.

The attribute data may additionally or alternatively be representative of recipient-specific information. For example, the attribute data may be representative of a preoperative assessment (e.g., an audiogram) of a hearing profile of the recipient, an age of the recipient, a size of the recipient's cochlea, etc.

The attribute data may additionally or alternatively be representative of an insertion depth for the electrode lead; an insertion speed at which the electrode lead is inserted into the cochlea, and/or or an insertion angle at which the electrode lead is inserted into the cochlea. Such data may be determined preoperatively (e.g.; based on historical data associated with a particular user). Additionally or alternatively, such data may be determined in real time during the lead insertion procedure in any suitable manner.

The attribute data may additionally or alternatively be representative of one or more preoperative images of the recipient's cochlea and/or a geometric model of the recipient's cochlea. The one or more preoperative images may be acquired using CT scans; a digital volume tomography (DVT) system, magnetic resonance imaging (MRI); ultrasound imaging, and/or any other suitable medical imaging technique. The geometric model may be generated in any suitable manner (e.g.; based on one or more preoperative images of the recipient's cochlea).

The attribute data may additionally or alternatively be representative of one or more intraoperative measurements performed with respect to the recipient during the lead insertion procedure. For example, the attribute data may be representative of a measurement of an evoked response elicited by stimulation (e.g., acoustic stimulation) of the recipient. Exemplary evoked responses include, but are not limited to, an electrocochleographic (ECochG) potential (e.g., a cochlear microphonic potential, a compound action potential such as an auditory nerve response, a summating potential, etc.), a brainstem response, a stapedius reflex, and/or any other type of neural or physiological response that may occur within a recipient in response to application of acoustic stimulation to the recipient. Evoked responses may originate from neural tissues, hair cell to neural synapses, inner or outer hair cells, and/or other sources.

The intraoperative measurement may additionally or alternatively include a measurement acquired by a sensor on the electrode lead. This sensor may include a force sensor, a pressure sensor, and/or any other type of sensor as may serve a particular implementation. For example, a force sensor and/or a pressure sensor may be configured to sense when the electrode lead is pressing against a wall of the cochlea.

The intraoperative measurement may additionally or alternatively include an ultrasound measurement, an optical sensor measurement, an electrical field sensor measurement, an electrode impedance measurement, and/or any other type of intraoperative measurement that may be performed by any suitable sensor and/or device.

The intraoperative measurement may additionally or alternatively include a scan of the cochlea that may be performed in any suitable manner. From this scan, rotational insertion of the electrode lead may be estimated through calculation of how far the linear extent of the electrode lead had made it around the curved wall of the cochlea.

System 700 (e.g., electrode selection module 904) may process attribute data in any suitable manner to select one or more electrodes for inclusion in the monitoring electrode set.

In some examples, system 700 may use a machine learning model to process the attribute data prior to electrode selection module 904 selecting electrodes for inclusion in the monitoring electrode set. This may advantageously allow system 700 to factor a number of attributes and/or combinations of attributes into the determination as to which electrodes should be dynamically included in the monitoring electrode set at any given time.

Figure 10:
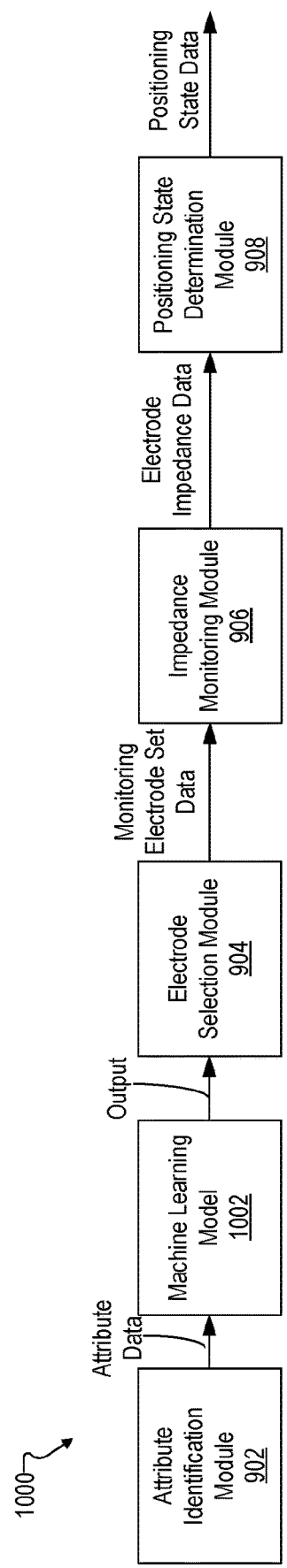

To illustrate, FIG. 10 shows an implementation 1000 of system 700 in which system 700 uses a machine learning model 1002 to process the attribute data generated by attribute identification module 902. Implementation 1000 is similar to implementation 900 in that both implementations include attribute identification module 902, electrode selection module 904, impedance monitoring module 906, and positioning state determination module 908. However, in FIG. 10, the attribute data generated by attribute identification module 902 is provided as an input to machine learning model 1002. Machine learning model 1002 may process the attribute data in any suitable manner. As shown, an output of machine learning model 1002 that takes into account the attribute data may be provided to electrode selection module 904. The output may be in any suitable form and/or format. Electrode selection module 904 may accordingly dynamically select one or more electrodes for inclusion in the monitoring electrode set based on the output of machine learning model 1002.

Machine learning model 1002 may be configured to perform any suitable machine learning heuristic (also referred to as artificial intelligence heuristic) with respect to input data (e.g., attribute data, as shown in FIG. 10). Machine learning model 1002 may be supervised and/or unsupervised as may serve a particular implementation and may be configured to implement one or more decision tree learning algorithms, association rule learning algorithms, artificial neural network learning algorithms, deep learning algorithms, bitmap algorithms, and/or any other suitable data analysis technique as may serve a particular implementation.

In some examples, machine learning model 1002 may be implemented by one or more neural networks, such as one or more deep convolutional neural networks (CNN) using internal memories of its respective kernels (filters), recurrent neural networks (RNN), and/or long/short term memory neural networks (LSTM). Machine learning model 1002 may be multi-layer. For example, machine learning model 1002 may be implemented by a neural network that includes an input layer, one or more hidden layers, and an output layer.

System 700 may access machine learning model 1002 in any suitable manner. For example, system 700 may store data representative of machine learning model 1002 in memory 702. Additionally or alternatively, data representative of machine learning model 1002 may be maintained by a system (e.g., one or more servers or other computing devices) remote from system 700. In these examples, system 700 may access machine learning model 1002 by communicating with the remote system by way of a network.

Figure 11:
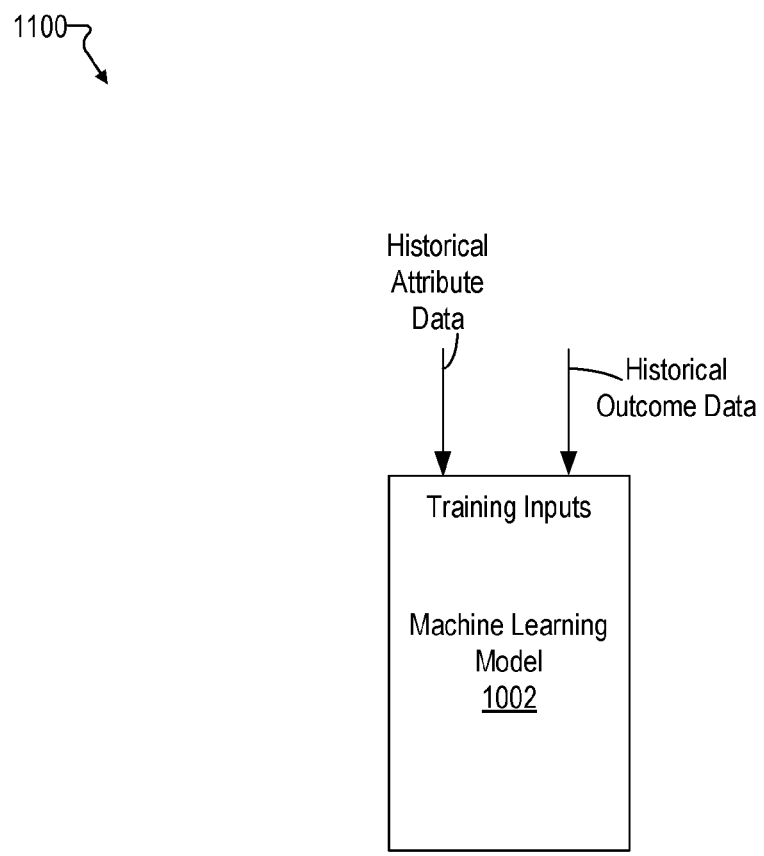
FIG. 11 shows an exemplary configuration in which a machine learning model is trained.

Machine learning model 1002 may be trained by system 700 or any other system in any suitable manner. For example, FIG. 11 shows an exemplary configuration 1000 in which system 700 (or a different system remote from system 700) is configured to provide various types of data as training inputs to machine learning model 1002. As shown, system 700 may provide historical attribute data and historical outcome data as training inputs to machine learning model 1002.

Each of the historical data training inputs shown in FIG. 10 may correspond to a plurality of cochlear implant recipients and lead insertion procedures. For example, each of the historical data training inputs may include data collected over a period of time (e.g., years) of the insertion procedures for various cochlear implant recipients at one or more clinics and as performed by one or more users (e.g., surgeons). For example, the historical attribute data may be representative of attributes of a plurality of lead insertion procedures in which electrode leads are inserted to the cochleas of the cochlear implant recipients and the historical outcome data may be representative of subjective and/or objective outcomes of the lead insertion procedures (e.g., lead insertion procedures in which translocation events and/or tip foldover events did not occur and lead insertion procedures in which translocation events and/or tip foldover events did occur). Based on this training data, machine learning model 1002 may learn how various combinations of factors related to a lead insertion procedure may combine to cause one or more positional states for an electrode lead.

As mentioned, system 700 may dynamically update which electrodes 804 are selected for inclusion in the monitoring electrode set. For example, electrodes 804-1 through 804-4 may be initially selected by system 700 for inclusion in the monitoring electrode set. Subsequently, based on a change in one or more attributes of the lead insertion procedure as described herein, which may cause a change in the output of machine learning model 1002, a different subset of electrodes (e.g., electrodes 804-4 through 804-7) may be selected for inclusion in the monitoring electrode set.

System 700 may be configured to monitor impedance values for electrodes included in a monitoring electrode set in any suitable manner. For example, system 700 may direct a cochlear implant to which electrode lead 802 is coupled to apply electrical stimulation (e.g., a stimulation pulse) by way of one or more electrodes 804 on electrode lead 802 and detect resultant voltages between electrodes included in the monitoring electrode set and a reference (e.g., a ground electrode on the electrode lead 802 and located outside the cochlea, a metal case of the cochlear implant, one of electrodes 804, etc.). The impedance values may be accordingly determined based on Ohm's law. Alternatively, it will be recognized that impedance values may be monitored simply by detecting voltages without actually calculating impedance values based on the detected voltages. Moreover, while reference is made in the examples herein to monitoring impedance values, any other physiologically generated signal may be monitored and used in a similar manner. In these cases, such physiologically generated signals may be measured by detecting voltages and/or other electrical characteristics. Hence, references made to monitoring impedances values herein may broadly refer to monitoring any physiologically generated signal using electrodes on an electrode lead. Such monitoring may be performed, for example, by measuring one or more voltages associated with the electrode (e.g., a voltage between an electrode and any of the references described herein, a voltage between two electrodes, etc.).

Various impedance measurement techniques that may be used by system 700 to detect impedance values for each electrode included in a monitoring electrode set will now be described. It will be recognized that other impedance measurement techniques may additionally or alternatively be used by system 700 in accordance with the principles described herein.

In one example, the monitoring electrode set for which system 700 monitors impedance values includes at least a first electrode (e.g., electrode 804-1), a second electrode (e.g., electrode 804-2), and a third electrode (e.g., electrode 804-2). In this example, system 700 may monitor the impedance values of the first, second, and third electrodes by sequentially and repeatedly measuring a first impedance value for the first electrode, a second impedance value for the second electrode, and a third impedance value for the third electrode in any of the ways described herein. Based on the second and third impedance values, system 700 may determine an expected impedance value for the first electrode. For example, system 700 may interpolate or otherwise process the second and third impedance values to establish the expected impedance value for the first electrode. It will be recognized that impedance values for any of the other electrodes in the monitoring electrode set may also be used to determine the expected value for the first electrode as may serve a particular implementation.

In this example, system 700 may be configured to detect an anomaly in the impedance values by comparing the first impedance value with the expected impedance value and determining, based on the comparison, that a difference between the first impedance value and the expected impedance value is greater than a threshold amount. For example, if the first impedance value is substantially higher than the expected impedance value, system 700 may output transaction log data indicating that the electrode lead (or at least the distal end of the electrode lead) is about to translocate or has translocated.

The threshold amount to which the difference between the first impedance value and the expected impedance value is compared may be set in any suitable manner. For example, system 700 may set the expected impedance value by establishing a baseline impedance value in any suitable manner, interpolating previous measured impedance values for the first electrode, determining a recipient-specific expected value based on one or more characteristics of the cochlea and/or electrode lead, etc.

As another example, system 700 may detect an impedance value for a particular electrode by directing a cochlear implant to apply electrical stimulation by way of the electrode and detect, in response to the application of the electrical stimulation by way of the electrode, a voltage between the electrode and a reference. The reference may be implemented in any of the ways described herein.

To illustrate, the monitoring electrode set for which system 700 monitors impedance values may include at least a first electrode (e.g., electrode 804-1) and a second electrode (e.g., electrode 804-2). In this example, system 700 may monitor an impedance value of the first electrode by directing the cochlear implant to apply electrical stimulation by way of the first electrode and detecting, in response to the applying of the electrical stimulation by way of the first electrode, a voltage between the first electrode and a reference. Subsequently, system 700 may apply electrical stimulation by way of the second electrode and detect, in response to the applying of the electrical stimulation by way of the second electrode, a voltage between the second electrode and the reference. System 700 may similarly detect impedance values for other electrodes included in the monitoring electrode set.

Additionally or alternatively, system 700 may use a cross impedance measurement technique to determine the impedance values for the electrodes in the monitoring electrode set. Cross impedance measurement techniques are described more fully in PCT Publication No. WO2019/045747, the contents of which are incorporated by reference in their entirety.

For example, system 700 may direct a cochlear implant to apply electrical stimulation on one electrode and record on (e.g., measure voltages at) the other electrodes in the monitoring electrode set, or apply electrical stimulation on all electrodes in the monitoring electrode set and record on another electrode (either in or out of the monitoring electrode set). System 700 may detect a decrease or an increase in cross-impedance (or a deviation from baseline established by more basal electrodes). For example, system 700 may stimulate on electrodes 804-1 804-2, 804-3, and 804-4 and record on electrode 804-5, The recording may include measuring a voltage between electrode 804-5 and a reference (e.g.; the electrode by which the electrical stimulation is applied or any of the other references described herein). Alternatively, system 700 may stimulate on 804-2, 804-3, 804-4, and 804-5 while recording on electrode 804-1. An advantage of this technique is that the recording electrode can remain constant, thereby speeding up the monitoring process.

In some examples, system 700 may measure an impedance value for a particular electrode (e.g., electrode 804-1) in the monitoring electrode set more frequently than impedance values for other electrodes (e.g., electrodes 804-2 through 804-4) included in the monitoring electrode set. Because switching between electrodes can be relatively slow, this may allow speed up of a most relevant acquisition sequence.

For example, in each measurement cycle, system 700 may determine which electrode to measure based on previous impedance value measurements. For example, electrode 804-1 can be recorded more frequently, while electrodes 804-2, 804-3, and 804-4 can be recorded less frequently and in an interleaved way. For example, the sequence can be as follows: 804-1, 804-1, 804-1, 804-2, 804-1, 804-1, 804-1, 804-3, 804-1, 804-1, 804-1, 804-4, etc.

Figure 12:
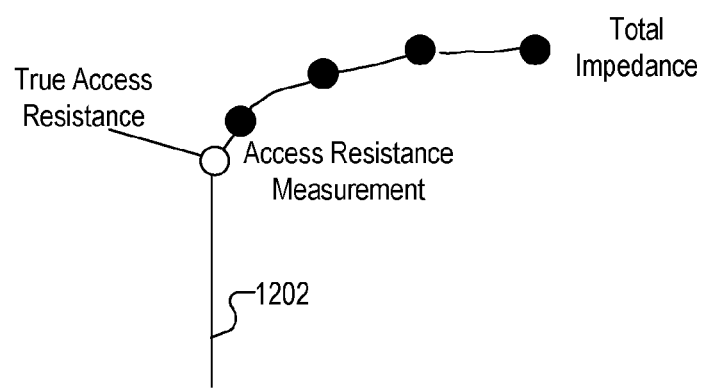
FIG. 12 illustrates an exemplary method.

System 700 may measure an impedance of an electrode in any suitable manner. For example, system 700 may measure a simple resistance (single point), or measure multiple points using a "super-sampling" concept. To illustrate, FIG. 12 shows various types of resistances that may be measured by system 700. Line 1202 represents a stimulation pulse applied by way of an electrode. System 700 may detect a true access resistance of the electrode (i.e., the "zero time" impedance that corresponds precisely to an occurrence of the pulse by measuring a few pulses with sampling offset between the pulses and then projecting down to the "zero time"). Alternatively, system 700 may measure the total impedance and/or determine an access resistance estimate in any suitable manner.

In some examples, system 700 may measure an impedance value for only a single electrode (e.g., 804-1). System 700 may compare the impedance of this electrode to past impedance values for the electrode. If the impedance value changes by more than a threshold amount, system 700 may provide a notification of possible translocation, tip foldover, and/or any other electrode lead insertion anomaly. Additionally or alternatively, when system 700 detects a change in impedance on the single electrode above a threshold, system 700 may dynamically add one or more additional electrodes to the monitoring electrode set for use in the monitoring. For example, system 700 may begin detecting impedances of other electrodes in the monitoring electrode set (e.g., electrodes 804-2, 804-3, and 804-4) to establish baseline and make a more accurate measurement. In this manner, time and resources may be conserved.

In some examples, the electrode impedance monitoring performed by system 700 may include identifying an anomaly in the impedance values for the electrodes included in the monitoring electrode set, Based on the anomaly, system 700 may determine that a translocation event, a tip foldover event, and/or any other incorrect electrode lead positioning event is about to occur or has occurred during the lead insertion procedure.

For example, system 700 may determine that a translocation event is about to occur or has occurred during the lead insertion procedure by determining that at least one of the impedance values varies from an expected impedance value by at least a threshold amount.

As another example, system 700 may determine that a tip foldover event is about to occur or has occurred during the lead insertion procedure by determining that a change in cross impedance between two electrodes included in the monitoring electrode set exceeds a threshold amount. For example, if tip foldover occurs, electrode 804-1 may be closer to electrode 804-4 than before the occurrence of tip foldover, thereby resulting in an increased cross impedance measurement between 804-1 and 804-4. This anomaly may be detected and used as an indicator that tip foldover has occurred.

Various ways in which system 700 may detect an anomaly in the impedance values of the electrodes included in the monitoring electrode set will now be described.

In one example, system 700 may detect an anomaly in the impedance values by comparing the impedance values to one or more baseline impedance values for the monitoring electrode set and determining, based on the comparison, that one or more of the impedance values differs by more than a threshold amount from one or more of the one or more baseline impedance values.

The one or more baseline impedance values to which the measured impedance values are compared may be determined in any suitable manner. For example, system 700 may determine the one or more baseline impedance values based on one or more previous impedance value measurements. To illustrate, system 700 may measure impedance values of the electrodes included in the monitoring electrode set as the electrodes are first being inserted into the cochlea. These initial impedance value measurements may be used to establish the one or more baseline impedance values against which subsequent impedance value measurements are compared.

Additionally or alternatively, system 700 may determine the one or more baseline impedance values based on one or more expected impedance value measurements. To illustrate, system 700 may access historical impedance value measurement data acquired during previously performed lead insertion procedures. Based on this historical impedance value measurement data, system 700 may determine one or more impedance values that are to be expected for one or more electrodes at different insertion depths. These expected impedance values may accordingly be used as baseline impedance values against which impedance value measurements acquired during the present lead insertion procedure are compared.

Additionally or alternatively, system 700 may determine the one or more baseline impedance values based on a preoperative image of the cochlea of the recipient, Based on this preoperative image, system 700 may identify one or more characteristics (e.g., size characteristics, shape characteristics, etc.) of the cochlea that may affect electrode impedance values during the lead insertion procedure. Based on the identified one or more characteristics, system 700 may determine baseline impedance values against which impedance value measurements acquired during the present lead insertion procedure are compared.

Additionally or alternatively, system 700 may determine the one or more baseline impedance values based on one or more characteristics of the electrode lead and/or recipient. For example, the baseline impedance values may be determined based on a particular make and model of electrode lead being used during the lead insertion procedure. As another example, the baseline impedance values may be determined based on an age of the recipient, a gender of the recipient, a size of the recipient, a preoperative hearing assessment (e.g., an audiogram) of the recipient, a preoperative image (e.g., a CT and/or MRI scan of the recipient's cochlea, temporal bones, etc.), and/or any other characteristic of the recipient as may serve a particular implementation.

As mentioned, system 700 may detect an anomaly in the impedance values of one or more measured impedance values differs by more than a threshold amount from one or more baseline impedance values. The threshold amount may be set in any suitable manner. For example, the threshold amount may be set based on one or more characteristics of the electrode lead and/or recipient.

To illustrate, system 700 may use fixed thresholds for impedance increase, or thresholds that are specific to a particular electrode design, or a particular point in the insertion process. In some examples, the thresholds may vary depending on the particular type of electrode lead that is being used. For example, different thresholds may be used for pre-curved electrode leads than for naturally straight electrode leads. In some examples, evoked response-based measurements, described herein, are used for one type of electrode lead (e.g., straight electrode leads) while impedance-based measurements are used for another type of electrode lead (e.g., pre-curved electrode leads).

In some examples, system 700 may maintain data representative of multiple threshold amounts. For example, system 700 may use a first relatively low threshold amount to determine that a translocation event and/or tip foldover event is about to occur. System 700 may use a second relatively high threshold amount to determine that a translocation event and/or tip foldover event has occurred.

To illustrate, a difference between a measured impedance value and a baseline impedance value may increase as the electrode lead starts on a translocation trajectory and then actually translocates. Hence, system 700 may provide a warning that a translocation event is about to occur if the difference between the measured impedance value and the baseline impedance value is above the first relatively low threshold amount. System 700 may then provide a warning that a translocation event has occurred if the difference between the measured impedance value and the baseline impedance value goes above the second relatively high threshold amount.

System 700 may be configured to perform any suitable operation based on a determined positioning state of an electrode lead.

For example, system 700 may present a notification indicating the positioning state of the electrode lead. System 700 may present the notification in any suitable manner. For example, system 700 may display the notification by way of a display device (e.g., within a graphical user interface displayed by the display device). To illustrate, system 600 may display the notification by way of a display device within a microscope used by a surgeon to perform the lead insertion procedure. In some examples, the display device may be included in an augmented reality system that produces a predicted image of the electrode lead's positioning state. Additionally or alternatively, system 700 may present an audible sound representative of the notification.

Additionally or alternatively, system 700 may be configured to provide, based on the translocation log data, one or more instructions regarding how to correct and/or prevent a translocation event, a tip foldover event, and/or any other incorrect positioning of the electrode lead. For example, system 700 may provide (e.g., display on a display device) one or more steps that may be performed to at least partially retract the electrode lead from the cochlea and then correctly reinsert the electrode lead into the cochlea.

Additionally or alternatively, system 700 may be configured to stop (e.g., automatically) the lead insertion procedure if a potentially harmful positioning state is detected. This may be performed in any suitable manner. For example, if a computer-assisted lead insertion system (e.g., a robotic lead insertion system) is being used to insert the electrode lead, system 700 may direct the computer-assisted lead insertion system to stop the lead insertion procedure (e.g., by transmitting one or more commands to the computer-assisted lead insertion system). System 700 may be further configured to transmit one or more additional commands to the computer-assisted lead insertion system to cause the electrode lead to be retracted until the electrode lead is no longer in the harmful positioning state.

In some examples, system 700 may be configured to detect potential trauma points within the cochlea and notify a user (e.g., a surgeon) of such trauma points as an electrode lead approaches them. For example, system 700 may use shape modelling data from a preoperative image (e.g., a CT or MRI scan) to predict potential trauma points. Such trauma points may include, but are not limited to, dips, bends, ossification, and/or other abnormalities in the cochlea.

In some examples, system 700 may track a positioning of the electrode lead as the electrode lead is being inserted (e.g., using any of the ways described herein). As the lead approaches a potential trauma point, system 700 may provide a warning to the surgeon. The warning may, for example, direct the surgeon to slow down the lead insertion procedure until the lead passes the potential trauma point.

In some examples, system 700 may be configured to detect extrusion of an electrode lead while a user is closing a flap (e.g., tissue) to cover the incision made to insert the electrode lead. For example, while a surgeon closes the flap, one or more electrodes may inadvertently slide out of the cochlea. To detect such extrusion, system 700 may perform a full (or partial) electric field imaging (EFI) test and determine whether one or more electrodes (e.g., electrodes located towards the basal end) have an EFI level that drops below a particular threshold. In response, system 700 may provide a notification indicating that extrusion may have occurred. For example, if the electrode lead has sixteen total electrodes, with electrode one being the most distal and electrode sixteen being the most proximal, and there is sharp drop in EFI level between electrodes fourteen and fifteen, this may be indicative that electrodes fifteen and sixteen are outside the cochlea.

As used herein, EFI refers to a process during which each electrode is stimulated in turn. During each stimulation event, a voltage is recorded on all electrodes.

In some examples, system 700 may measure EFI while stimulating with respect to the case of the cochlear implant, a ring electrode on the electrode lead and configured to remain outside the cochlea after the distal portion of the electrode lead is inserted into the cochlea, and/or both grounds together. In so doing, system 700 may predict a likelihood of non-auditory stimulation (e.g., stimulation of a location outside the auditory pathway). Due to its positioning, the ring ground is more likely to pull current out back out the cochlea. In contrast, the case ground is more likely to pull current through walls of cochlea. Hence, EFI may be measured using each ground separately, and with both enabled at the same time. The results may be compared to determine a likelihood of non-auditory stimulation and/or information about the electrode's location in the cochlea.

In some examples, system 700 may be configured to determine a baseline electrode location map indicative of a positioning of electrodes within the cochlea once a lead insertion procedure is complete. This baseline electrode location map may be useful at a future time when, for example, it may be compared to a subsequently determined electrode location map to determine electrode migration, etc. and compensate accordingly.

For example, system 700 may be determine the baseline electrode location map by including a single supra-threshold amplitude NRI measure (or any other evoked response measure) on a number of electrode contacts (e.g., every odd numbered contact) and a single spread of excitation NRI measurement on one contact. These would contribute to a baseline measure for establishing electrode location. Evoked response elicitation is described in more detail in PCT Publication No. WO2019/045680, the contents of which are incorporated by reference in their entirety.

Any of the measurement techniques and/or features described herein may be optionally enabled or disabled depending on a particular surgeon's insertion technique, time available, residual hearing in the ear, perceived anatomical risk prior to surgery, and/or any other factor. In some examples, system 700 may assess one or more of these factors and generate automatic recommendation based on the assessment. A user may accept or override the recommendation.

Figure 13:
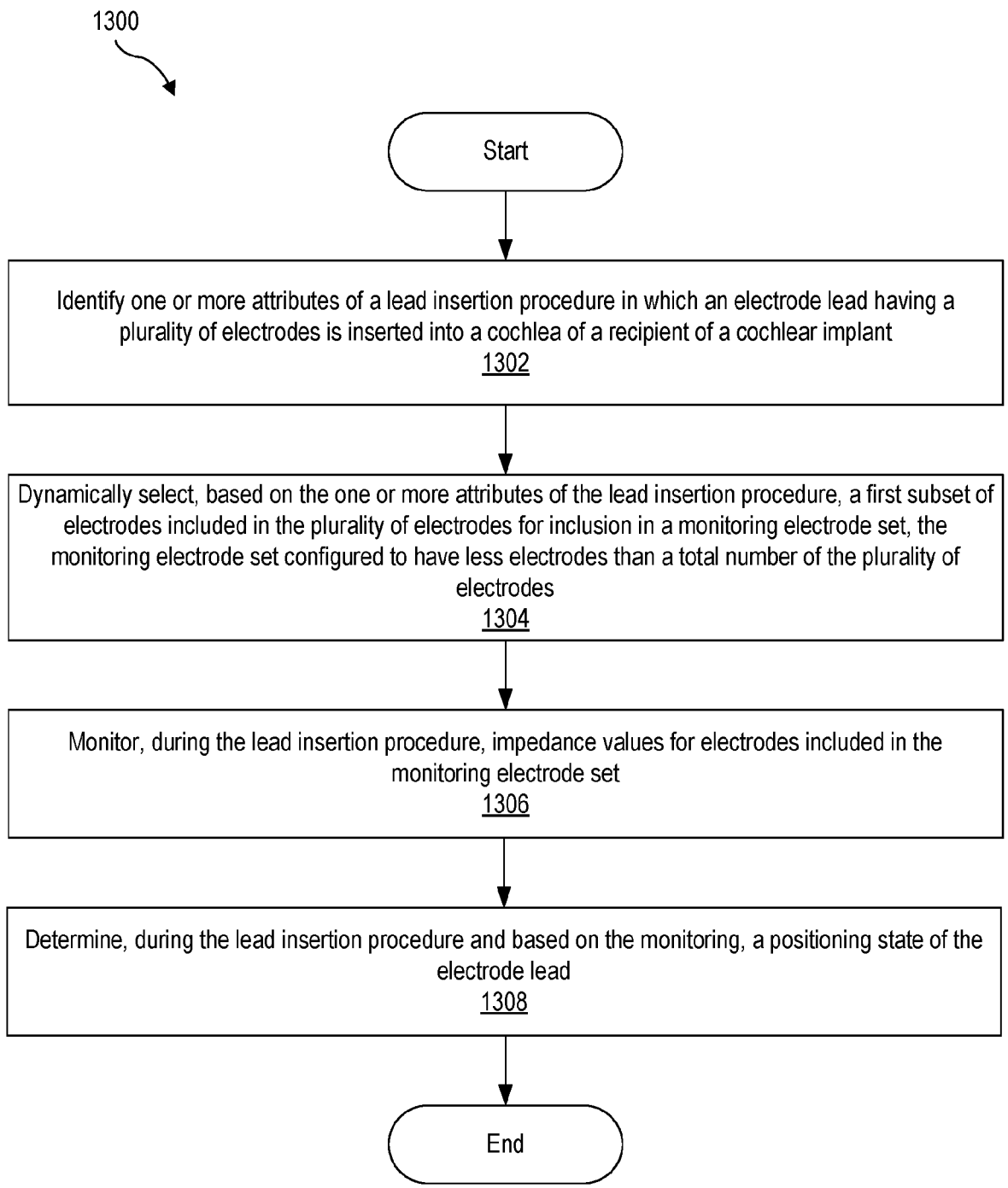
FIG. 13 illustrates an exemplary computing device.

FIG. 13 illustrates an exemplary method 1300 that may be performed by an insertion management system (e.g., system 700 or any implementation thereof, such as at least one computing device). While FIG. 13 illustrates exemplary operations according to one embodiment, other embodiments may omit, add to, reorder, and/or modify any of the operations shown in FIG. 13. Each of the operations shown in FIG. 13 may be performed in any of the ways described herein.

At operation 1302, an insertion management system identifies one or more attributes of a lead insertion procedure in which an electrode lead having a plurality of electrodes is inserted into a cochlea of a recipient of a cochlear implant.

At operation 1304, the insertion management system dynamically selects, based on the one or more attributes of the lead insertion procedure, a first subset of electrodes included in the plurality of electrodes for inclusion in a monitoring electrode set. The monitoring electrode set is configured to have less electrodes than a total number of the plurality of electrodes.

At operation 1306, the insertion management system monitors, during the lead insertion procedure, impedance values for electrodes included in the monitoring electrode set.

At operation 1308, the insertion management system determines, during the lead insertion procedure and based on the monitoring, a positioning state of the electrode lead.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 14:
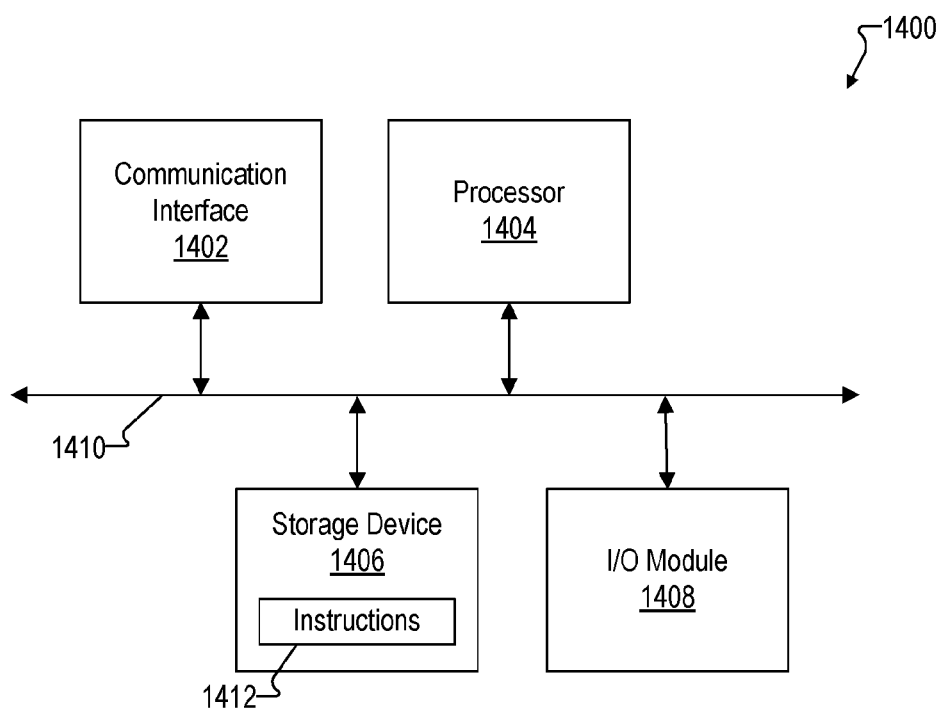

FIG. 14 illustrates an exemplary computing device 1400 that may be specifically configured to perform one or more of the processes described herein. To that end, any of the systems, processing units, and/or devices described herein may be implemented by computing device 1400.

As shown in FIG. 14, computing device 1400 may include a communication interface 1402, a processor 1404, a storage device 1406, and an input/output ("I/O") module 1408 communicatively connected one to another via a communication infrastructure 1410, While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data and/or interpreting, executing, and/or directing execution of one or more of the instructions, processes, and/or operations described herein. Processor 1404 may perform operations by executing computer-executable instructions 1412 (e.g., an application, software, code, and/or other executable data instance) stored in storage device 1406.

Storage device 1406 may include one or more data storage media, devices, or configurations and may employ any type, form, and combination of data storage media and/or device. For example, storage device 1406 may include, but is not limited to, any combination of the non-volatile media and/or volatile media described herein. Electronic data, including data described herein, may be temporarily and/or permanently stored in storage device 1406. For example, data representative of computer-executable instructions 1412 configured to direct processor 1404 to perform any of the operations described herein may be stored within storage device 1406. In some examples, data may be arranged in one or more databases residing within storage device 1406.

I/O module 1408 may include one or more I/O modules configured to receive user input and provide user output. I/O module 1408 may include any hardware, firmware, software, or combination thereof supportive of input and output capabilities. For example, I/O module 1408 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
 identify, prior to a commencement of a lead insertion procedure in which an electrode lead having a plurality of an electrodes is to be inserted into a cochlea of a recipient of a cochlear implant, one or more attributes of the lead insertion procedure;
 dynamically select, based on the one or more attributes of the lead insertion procedure as identified prior to the commencement of the lead insertion procedure, a first subset of electrodes included in the plurality of electrodes for inclusion in a monitoring electrode set, the monitoring electrode set configured to have less electrodes than a total number of the plurality of electrodes;

monitor, during the lead insertion procedure, impedance values for electrodes included in the monitoring electrode set; and determine, during the lead insertion procedure and based on the monitoring, a positioning state of the electrode lead.

2. The system of claim 1, wherein the one or more attributes comprise one or more of a characteristic of the electrode lead, a characteristic of a tool being used to insert the electrode lead into the cochlea, a characteristic of an opening in the recipient through which the electrode lead is to be inserted, an identity of a user performing the lead insertion procedure, a surgical tendency of the user performing the lead insertion procedure, a preoperative assessment of a hearing profile of the recipient, a preoperative image of the cochlea of the recipient, a geometrical model of the cochlea of the recipient, or an intraoperative measurement performed during the lead insertion procedure.

3. The system of claim 1, wherein:
the processor is further configured to execute the instructions to provide, as an input to a machine learning model, attribute data representative of the one or more attributes; and
the dynamically selecting of the first subset of electrodes is based on an output of the machine learning model that takes into account the attribute data.

4. The system of claim 3, wherein the machine learning model is trained by applying historical attribute data representative of one or more attributes of a plurality of lead insertion procedures in which electrode leads are inserted into cochleas of a plurality of cochlear implant recipients.

5. The system of claim 1, wherein the processor is further configured to execute the instructions to
perform, during the lead insertion procedure, one or more intraoperative measurements;
determine, based on the one or more intraoperative measurements, one or more additional attributes.

6. The system of claim 1, wherein:
the monitoring comprises identifying an anomaly in the impedance values; and
the determining of the position state comprises determining, based on the anomaly, that a translocation event in which the electrode lead translocates from a first scala of the cochlea to a second scala of the cochlea is about to occur or has occurred during the lead insertion procedure.

7. The system of claim 5, wherein the processor is further configured to execute the instructions to:
detect a change in the one or more attributes during the lead insertion procedure; and
dynamically update, based on the change in the one or more attributes, the monitoring electrode set to have a second subset of the plurality of electrodes, the second subset having at least one electrode not included in the first subset.

8. The system of claim 5, wherein:
the processor is further configured to execute the instructions to provide, as an input to a machine learning model, attribute data representative of the one or more attributes; and
the dynamically updating of the monitoring electrode set is based on an output of the machine learning model that takes into account the attribute data.

9. The system of claim 8, wherein the identifying of the anomaly comprises determining that at least one of the impedance values varies from an expected impedance value by at least a threshold amount.

10. The system of claim 1, wherein:
the monitoring comprises identifying an anomaly in the impedance values; and
the determining of the position state comprises determining, based on the anomaly, that a tip foldover event in which a distal tip of the electrode lead folds over within the cochlea is about to occur or has occurred during the lead insertion procedure.

11. The system of claim 10, wherein the identifying of the anomaly comprises determining that a change in cross impedance between two electrodes included in the monitoring electrode set exceeds a threshold amount.

12. The system of claim 1, wherein the determining of the position state comprises determining, based on the monitoring, that the electrode lead is correctly positioned within the cochlea during the lead insertion procedure.

13. The system of claim 1, wherein:
the monitoring electrode set comprises at a first electrode and a second electrode; and
the monitoring of the impedance values comprises:
directing the cochlear implant to apply electrical stimulation by way of the first electrode;
detecting, in response to the applying of the electrical stimulation by way of the first electrode, a voltage between the first electrode and a reference;
directing, subsequent to the applying of the electrical stimulation by way of the first electrode, the cochlear implant to apply the electrical stimulation by way of the second electrode; and
detecting, in response to the applying of the electrical stimulation by way of the second electrode, a voltage between the second electrode and the reference.

14. The system of claim 1, wherein:
the monitoring electrode set comprises at a first electrode and a second electrode; and
the monitoring of the impedance values comprises:
directing the cochlear implant to apply electrical stimulation by way of the first electrode, and
detecting, in response to the applying of the electrical stimulation by way of the first electrode, a voltage between the second electrode and a reference.

15. The system of claim 1, wherein the monitoring electrode set includes no more than four electrodes.

16. The system of claim 1, wherein the processor is further configured to execute the instructions to present a notification indicating the positioning state of the electrode lead.

17. A method comprising:
identifying, by an insertion management system prior to a commencement of a lead insertion procedure in which an electrode lead having a plurality of electrodes is inserted into a cochlea of a recipient of a cochlear implant, one or more attributes of the lead insertion procedure;
dynamically selecting, by the insertion management system based on the one or more attributes of the lead insertion procedure as identified prior to the commencement of the lead insertion procedure, a first subset of electrodes included in the plurality of electrodes for inclusion in a monitoring electrode set, the monitoring electrode set configured to have less electrodes than a total number of the plurality of electrodes;

monitoring, by the insertion management system during the lead insertion procedure, impedance values for electrodes included in the monitoring electrode set; and determining, by the insertion management system during the lead insertion procedure and based on the monitoring, a positioning state of the electrode lead.

18. A non-transitory computer-readable medium storing instructions that, when executed, direct a processor of a computing device to:

identify prior to a commencement of a lead insertion procedure in which an electrode lead having a plurality of electrodes is inserted into a cochlea of a recipient of a cochlear implant, one or more attributes of the lead insertion procedure;

dynamically select, based on the one or more attributes of the lead insertion procedure as identified prior to the commencement of the lead insertion procedure, a first subset of electrodes included in the plurality of electrodes for inclusion in a monitoring electrode set, the monitoring electrode set configured to have less electrodes than a total number of the plurality of electrodes;

monitor, during the lead insertion procedure, impedance values for electrodes included in the monitoring electrode set; and determine, during the lead insertion procedure and based on the monitoring, a positioning state of the electrode lead.

19. The system of claim 7, wherein the dynamically selecting the first subset of electrodes is further based on the one or more additional attributes.

20. The system of claim 7, wherein the one or more additional attributes comprises at least one of an insertion depth for the electrode lead, an insertion speed at which the electrode lead is inserted into the cochlea, an insertion angle at which the electrode lead is inserted into the cochlea, or an impedance value for one or more of the plurality of electrodes.

* * * * *